(12) United States Patent
Garcia-Perez et al.

(10) Patent No.: US 9,790,115 B2
(45) Date of Patent: Oct. 17, 2017

(54) PROCESSING BIOMASS USING THERMOCHEMICAL PROCESSING AND ANAEROBIC DIGESTION IN COMBINATION

(75) Inventors: Manuel Garcia-Perez, Pullman, WA (US); Craig Frear, Pullman, WA (US)

(73) Assignee: Washington State University, Pullman, WA (US)

( * ) Notice: Subject to any disclaimer, the term of this patent is extended or adjusted under 35 U.S.C. 154(b) by 413 days.

(21) Appl. No.: 13/483,493

(22) Filed: May 30, 2012

(65) Prior Publication Data

US 2012/0322130 A1 Dec. 20, 2012

Related U.S. Application Data

(60) Provisional application No. 61/491,253, filed on May 30, 2011.

(51) Int. Cl.
| | | |
|---|---|---|
| C02F 11/04 | (2006.01) | |
| C12P 5/02 | (2006.01) | |
| C12M 1/107 | (2006.01) | |
| C12M 1/00 | (2006.01) | |
| C10G 1/02 | (2006.01) | |
| C02F 11/10 | (2006.01) | |
| C02F 103/28 | (2006.01) | |

(52) U.S. Cl.
CPC ............ *C02F 11/04* (2013.01); *C10G 1/02* (2013.01); *C12M 21/04* (2013.01); *C12M 43/00* (2013.01); *C12M 45/20* (2013.01); *C12M 47/00* (2013.01); *C12P 5/023* (2013.01); *C02F 11/10* (2013.01); *C02F 2103/28* (2013.01); *Y02E 50/343* (2013.01); *Y02P 30/20* (2015.11); *Y02W 10/23* (2015.05)

(58) Field of Classification Search
CPC ...... C02F 11/04; C02F 11/10; C02F 2103/28; Y02E 50/343; C12P 5/023; C12M 21/04; C12M 43/00; C12M 45/20; C12M 47/00; C10G 1/02; Y02P 30/20; Y02W 10/23
USPC ................................ 435/289.1, 283.1–309.4
See application file for complete search history.

(56) References Cited

U.S. PATENT DOCUMENTS

| | | | |
|---|---|---|---|
| 6,048,374 A | 4/2000 | Green | |
| 2007/0117195 A1* | 5/2007 | Warner et al. | 435/161 |
| 2007/0217995 A1* | 9/2007 | Matsumura et al. | 423/657 |

(Continued)

FOREIGN PATENT DOCUMENTS

WO 2010-001137 1/2010

OTHER PUBLICATIONS

S.B. Jones et al.; "Production of Gasoline and Diesel from Biomass via Fast Pyrolysis, Hydrotreating and Hydrocracking: A Design Case"; U.S. Department of Energy, PNNL-18284, Feb. 28, 2009, entire document.

*Primary Examiner* — Gautam Prakash
(74) *Attorney, Agent, or Firm* — Whitham, Curtis & Cook, P.C.

(57) ABSTRACT

Systems and methods for integrating thermochemical processing of biomass and anaerobic digestion are provided. Light oxygenated organic compounds are produced as byproducts of thermochemical biomass processing e.g. by torrefaction and/or pyrolysis, and are converted to methane by anaerobic digestion. Thermochemical processing units may or may not be co-located with the anaerobic digestion units, with co-location providing benefits for e.g. rural agricultural enterprises.

14 Claims, 5 Drawing Sheets

(56) References Cited

U.S. PATENT DOCUMENTS

| | | | |
|---|---|---|---|
| 2009/0151253 A1* | 6/2009 | Manzer et al. | 48/62 R |
| 2009/0229595 A1 | 9/2009 | Schwartz, Jr. | |
| 2010/0133085 A1 | 6/2010 | Hutchins et al. | |
| 2011/0179700 A1* | 7/2011 | Monroe et al. | 44/589 |
| 2011/0245489 A1* | 10/2011 | Steele et al. | 536/124 |

* cited by examiner

PROCESSING BIOMASS USING THERMOCHEMICAL PROCESSING AND ANAEROBIC DIGESTION IN COMBINATION

CROSS-REFERENCE TO RELATED APPLICATIONS

This application claims benefit of U.S. provisional patent application 61/491,253, filed May 30, 2011, the complete contents of which is hereby incorporated by reference.

This invention was made with government support under grant number 2010-38502-21839 awarded by the United States Department of Agriculture through the National Institute of Food and Agriculture. The government has certain rights in this invention.

BACKGROUND OF THE INVENTION

Field of the Invention

The invention generally relates to systems and methods for integrating thermochemical processing of biomass (e.g., lignocellulosic materials) and anaerobic digestion. In particular, the invention provides systems and methods in which the byproducts of thermochemical biomass processing (e.g., torrefaction, pyrolysis, gasification) procedures such as light oxygenated organic compounds, are converted to methane by anaerobic digestion.

Background of the Invention

Thermochemical processing of lignocellulosic plant material (e.g., torrefaction, pyrolysis, and gasification) is of great interest with respect to developing alternative energy sources. These processes employ heat and catalysts to transform plant material into useful fuels which can replace traditional fuels such as oil and coal. The plant matter that is processed may be purposefully obtained for thermochemical processing, or may be "waste" material or a byproduct from other processes. Waste and byproducts are especially attractive for use, since this eliminates the need for their disposal, and instead converts them to useful substances.

During the pyrolysis of lignocellulosic materials, a sizable fraction of the biomass (8-15 mass %) is converted into light oxygenated organic compounds. These small organic compounds can be condensed and recovered in the form of an aqueous fraction containing between 10-50 mass % of organics. Formic acid, acetic acid, propionic acid, methanol (wood alcohol), glycoaldehyde, and acetol are the main light oxygenated organic compounds produced by thermochemical processing. These small organic compounds can also be produced during the torrefaction and gasification of lignocellulosic materials.

During the 19th and the 20th centuries most of the methanol, acetic acid and acetone consumed in the world was produced by refining aqueous fractions produced by the slow pyrolysis of wood (wood distillation). With the creation and expansion of the petroleum industry in the first half of the 20th century and with the development of cheaper catalytic routes to produce methanol, the interest in producing and utilizing light oxygenated organic compounds via biomass thermochemical processing disappeared. In fact, the production of these small molecules is currently considered a serious environmental problem, limiting the deployment of pyrolysis and torrefaction units for bio-fuel and bio-power production. There is a need in the art for efficient and cost effective means for processing the light organic materials produced from thermochemical processing. This could be a boon to the alternative energy field by solving the problem of disposal of the byproducts of thermochemical bio-fuel generation.

SUMMARY OF THE INVENTION

Anaerobic digestion provides an excellent opportunity to convert light organic small molecule materials produced from thermochemical processing, which otherwise have limited market value, into the useful and valuable commodity methane. Incorporating anaerobic digestion capabilities into thermochemical processing facilities solves the "problem" of disposing of thermochemical byproducts, while advantageously producing a desirable product. In addition, the combined technologies can be adapted for either large or small scale use. For example, co-locating anaerobic digestion systems with plant and/or animal agricultural operations that use thermochemical processing of plant and/or animal waste efficiently provides for disposal/use of the waste via thermochemical processing (which itself produces useful fuels) and the disposal/use of the byproducts of thermochemical processing to produce methane. Methane that is so produced can be employed as fuel, e.g. by being recycled back into the system to provide fuel for thermochemical processing, or for other purposes. Alternatively, the methane may be used for hydrogen production e.g. via steam reforming. The integrated systems described herein are cost effective and can serve to spur economic development and adoption of alternative fuel technologies. This can be especially valuable in rural farm settings and/or in rural bio-oil refineries, where the elimination of waste and opportunities to increase agricultural profits are a prime concern.

It is an object of this invention to provide a system for the processing at least one biomass source. The system comprises 1) an anaerobic digester suitable for the digestion of low solid content biomass; 2) at least one thermochemical reactor suitable for the controlled degradation of high solid content biomass; 3) a fractional condenser system suitable to separate fractions produced by the thermochemical reactor; and 4) a transfer system to transport at least one fraction produced in the thermochemical reactor into the anaerobic digester. In some embodiments, the thermochemical reactor is a torrefaction reactor. In additional embodiments the torrefaction reactor is configured to yield a solid torrefied biomass and an aqueous fraction containing oxygenated organic compounds for transfer into the anaerobic digester. In some embodiments, the solid torrefied biomass is pelleted. In other embodiments, the thermochemical reactor is a pyrolysis reactor. The pyrolysis reactor may be configured to yield char in addition to liquid fractions. In some embodiments, the fractional condenser system comprises a plurality of condensers each configured to concentrate a distinct fraction of the hydrocarbons produced by the pyrolysis reactor. The distinct fraction may comprise a bio-oil that is not transferred into the anaerobic digester. In other embodiments, the fractional condenser system is configured to separate a fraction of light oxygenated organic compounds and water. In additional embodiments, the fractional condenser system comprises a plurality of condensers each configured to concentrate a distinct fraction produced by the thermochemical reactor. In some embodiments, the thermochemical reactor and condenser system are geographically isolated from the anaerobic digester. In other embodiments, the transfer system is automotive, rail, air, pipeline and/or a combination thereof. In yet other embodiments, the anaerobic digester is configured such that at least a fraction of methane produced by the anaerobic digester is utilized to produce a chemical needed to up-grade the bio-oil. In yet other embodiments, the anaerobic digester is configured such that methane produced in the anerobic digester is steam reformed to produce hydrogen. Some embodiments include a means to direct produced hydrogen for use in the hydrotreatment of a bio-oil. In other embodiments, a fraction transferred into the anaerobic digester comprises light oxygenated organic compounds. In some embodiments, the thermochemical reactor is a two stage reactor comprising a first torrefaction stage and a second pyrolysis stage. In other embodiments, the anaerobic digester is configured such that at least a fraction of the methane produced by the anaerobic digestion is burned to generate energy and/or heat. In yet other embodiments, at least a fraction of the energy and/or heat produced is consumed by the thermochemical reactor. In other embodiments, the at least a fraction of the energy and/or heat produced is consumed by a co-located agricultural operation.

The invention further provides a method for biomass conversion comprising: 1) thermochemical treatment of a high solid biomass to yield a biomass solid and an aqueous fraction comprising oxygenated organic compounds; and 2) anaerobic digestion of a low solid biomass and said aqueous fraction to yield methane. Some embodiments include a step of separating fractions from said thermochemical treatment using one or more condensers.

DETAILED DESCRIPTION

Figure 1:
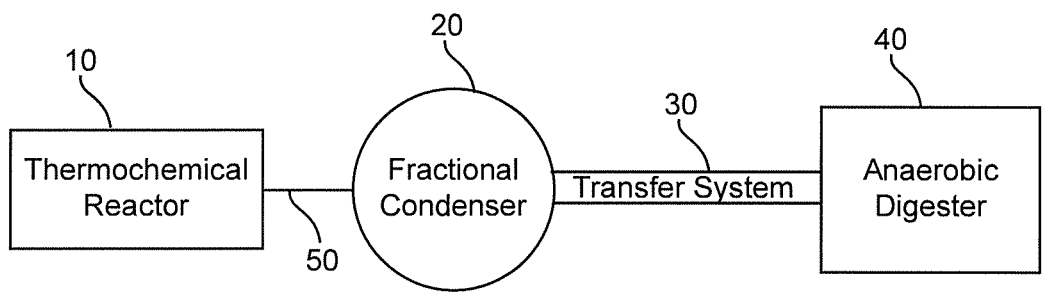
FIG. 1. Schematic illustration of the combined thermochemical processing and anaerobic digestion system of the invention.

The present invention solves the problem of disposal of "waste stream" products generated by thermochemical processing of lignocellulosic materials. The invention provides integrated systems which incorporate both thermochemical processing capabilities and anaerobic digestion capabilities. Anaerobic digestion is used to convert the byproducts of thermochemical processing to methane.

Definitions:

The following definitions are used throughout:

Biomass: as used herein, biomass refers to plant or animal matter, including waste, that can be used as a source of energy as described herein. In some embodiments, the biomass is plant matter comprising e.g. cellulose, hemicellulose, lignin, etc. Sources of biomass include, for example, wood, plants, algae, grass, solid animal waste, etc.

High solids biomass: High solid content biomass comprises low moisture content solids (e.g. solid with less than about 50% water by mass). Sources of low moisture content solids include but are not limited to: woody biomass, municipal wastes, agricultural materials, food scraps, fiber extruded from anaerobic digesters, and mixtures thereof. In the preferred embodiment the low solid content biomass is lignocellulosic material.

Low solids biomass: Low solids content biomass comprises an aqueous organic material containing less than about 20% by mass of solid materials. Sources of organic material to be used as low solids biomass include but are not limited to: animal waste, municipal wastes, sludge from wastewater treatment, agricultural materials, wastes from processing of biological materials, food scraps, and mixtures thereof, etc.

Thermochemical reactor is closed reactor vessel in which biomass is heated in a controlled manner in the presence or absence of an oxidizing agent to yield water, volatile organic chemicals and a thermally treated solid biomass (Bridgewater 1999, 2000, 2003, 2011, Czernik and Bridgewater 2004, Mohan et al 2006). Exemplary thermochemical reactors include torrefaction reactors and pyrolysis reactors. A thermochemical reactor unit as used herein may comprise one or more thermochemical reactors and/or one or more types of thermochemical reactors.

Torrefaction: a thermochemical treatment of high solids biomass carried out under atmospheric pressure and in the absence of oxygen at from about 150 to 350° C., e.g. between about 150-320° C., or about 200-320° C., or about 200-300° C. or about 150-300° C. During the torrefaction process, the water contained in the biomass is removed, and the biopolymers which make up the high solids biomass (e.g. cellulose, hemicellulose, lignin) partly decompose giving off various types of volatiles (e.g. $H_2$, $CH_4$). Torrefaction thus yields water, volatile organic compounds and a solid, dry, blackened material which is referred to as "torrefied biomass" or "bio-coal". During torrefaction, the biomass typically loses between 20 and 40% of its mass but only 10-20% of its energy content. Some of the "lost" energy is present in the volatiles, which can be collected and used, e.g., as a heating fuel for the torrefaction process itself, or for other purposes such as those described herein. The remaining (80-90%) energy content is present in the torrefied biomass, which can be used as fuel. For example, the torrefied biomass may be ground and fed into a second thermochemical reactor or may be densified, usually into briquettes or pellets, to yield energy dense biomass that can be subsequently burned for heat of electricity generation. (See, e.g., Weisselberg et al US 2010/0083530 A1, Reed US 2003/0221363 A1, and Stromberg et al US 2011/0041392 A1, each of which are incorporated herein by reference). Densification also improves the hydrophobic properties of the torrefied biomass. In contrast to the original biomass, torrefied biomass is very dry and very hydrophobic and is thus generally inhospitable to microbes. Torrefied biomass can therefore be conveniently stored in moist air, rain, etc. without rotting. Torrefaction is thus used to produce high-grade solid bio-fuels from various streams of low-grade biomass.

Pyrolysis refers to the thermochemical decomposition of organic material at elevated temperatures without the presence of an oxidizing agent (example oxygen), e.g. at from about 300-500° C., or from about 350-450° C., or from about 400-450° C., or at least above about 300° C., depending on the type of biomass being treated, the desired products, etc. It involves the simultaneous change of chemical composition and physical phase, and is irreversible. Pyrolysis yields water, light organic compounds, heavy organic compounds which have potential for the production of transportation fuels and char (e.g., "bio-char"). The light organic compounds are generally chemicals with fewer than five carbon atoms (e.g. light oxygenated organics) while the heavy organic compounds are chemicals with five or greater carbon atoms (e.g., bio-oil). There are a number of methods for pyrolysis systems and techniques known the art, including but not limited to: published US patent application 2010/0223839 to Garcia-Perez et al.; Bridgewater (1999, 2000, 2003, 2011); Czernik and Bridgewater, 2004; and Mohan et al., 2006, each of which are incorporated herein by reference. Pyrolysis is the basis of several methods that are being developed for producing fuel from biomass, which may include either crops grown for the purpose or biological waste products from other industries. Bio-oil produced by pyrolysis can be used as a fuel, typically after the removal of valuable bio-chemicals that can be used as food additives or pharmaceuticals. Higher efficiency is achieved by the so-called flash pyrolysis, in which finely divided feedstock is quickly heated to between 350 and 500° C. for less than 2 seconds. Fuel bio-oil resembling light crude oil can also be produced by hydrous pyrolysis from many kinds of feedstock, including waste from pig and turkey farming, by a process called thermal depolymerization (which may, however, include other reactions besides pyrolysis). Some of the most common pyrolysis reactors used in the field are: fixed bed, fluidized bed, circulating bed, ablative, rotary drums, moving beds, and Auger reactors.

Fractional condenser refers to a condenser which is utilized to selectively separate a component (or components) of the products of a thermochemical process from the other components. In certain embodiments, a single condenser separates a mixture of the water and light oxygenated organic compounds. In other embodiments two or more condensers operate in series to first separate a fraction containing a bio-oil and a second fraction containing water and light oxygenated organic compounds. Fractional condenser designs and methods of their use are known in the art, and many have been tailored for the separation of light and heavy organic fractions from thermochemical processing of biomass (See, e.g., Bunbury 1926, Oasmaa et al 2005, Westerhof et al 2007, 2011, each of which are herein incorporated by reference).

Aqueous fraction: the liquid fraction from thermochemical processing which contains light oxygenated organic compounds, and which is added to an anaerobic digester for co-digestion by the anaerobes therein. Light oxygenated organic compounds are hydrocarbons that have fewer than 5 carbon atoms and at least one oxygen atom. Examples include but are not limited to formic acid, acetic acid, propionic acid, methanol, glycoaldehyde, acetol, etc.

Bio-oil is a liquid fraction containing oxygenated organic molecules and water (<20% w/w) that is obtained from pyrolysis. In this document, bio-oil is referred to as the liquid separated from the reaction products of a pyrolysis reactor via a fractional condenser. A bio-oil typically contains oxygenated organic compounds that have five or more carbon atoms. Bio-oil's are often unstable and degrade over time. This limits their utility in traditional petrochemical processing because often the transport of bio-oil is required for economical integration. Bio-oil's can be stabilized or "up-graded" through processes such as hydrotreatment.

Hydrotreatment is a generic term indicating the use of hydrogen and one or more appropriate catalysts to remove undesirable components (O, N, S) from refinery streams. In the case of bio-oil hydrotreatment, the hydrogen stabilizes reactive groups, removes some oxygen or saturates some unsaturated bonds. (see, e.g., Venderbosch et al. 2009; Wildschut et al 2010; de Miguel Mercader 2010a, 2010b; Wildschut 2011; Jones et al 2009; and Elliott et al. 2007, 2009, each of which are herein incorporated by reference).

Anaerobic digestion is a series of processes in which microorganisms break down biodegradable material in the absence of oxygen. The digestion process begins with bacterial hydrolysis of the input materials to break down insoluble organic polymers, such as carbohydrates, and make them available for other bacteria. Acidogenic bacteria then convert the sugars and amino acids into carbon dioxide, hydrogen, ammonia, and organic acids. Acetogenic bacteria then convert these resulting organic acids into acetic acid, along with additional ammonia, hydrogen, and carbon dioxide. Finally, methanogens (e.g. methanogenic archaea) convert these products to methane and carbon dioxide.

Exemplary Integrated Systems of the Invention

Herein, we propose systems and methods for the co-digestion of the light oxygenated organic compounds produced by the thermochemical processing of biomass (e.g., lignocellulosic materials) in a newly designed anaerobic digester for the production of methane. According to an embodiment of the invention, the aqueous fractions rich in light oxygenated organic compounds produced by thermochemical processing (e.g., torrefaction, pyrolysis or gasification) are recovered and passed to an anaerobic digester for co-digestion with the feed stock that is being used in the digester, as described by example in detail below.

The integrated anaerobic digester systems of the invention are represented schematically in FIG. 1. With reference to FIG. 1, the systems comprise an anaerobic digester 40 suitable for the digestion of low solid content biomass; thermochemical reactor 10 suitable for the controlled degradation of high solid content biomass; a fractional condenser system 20 suitable to condense fractions produced by the thermochemical reactor; and a transfer system 30 to transport at least one fraction so produced to anaerobic digester 40. The system may optionally comprise transfer system 50 for transporting products (e.g. gases, volatiles) produced in thermochemical reactor 10 to fractional condenser 20 (which may be referred to simply as a "condenser" herein) for condensation. Alternatively, fractional condenser 20 may be "built in" to thermochemical reactor 10.

Optionally, the system may also include units capable separating the components of a mixture (e.g. the aqueous fraction, which contains multiple light organic molecules) into components via fractional distillation.

Exemplary Thermochemical Processes

Torrefaction Reactors

Exemplary thermochemical processes which can be coupled to anaerobic digestion in the systems of the invention include but are not limited to torrefaction, pyrolysis and gasification.

Figure 2:
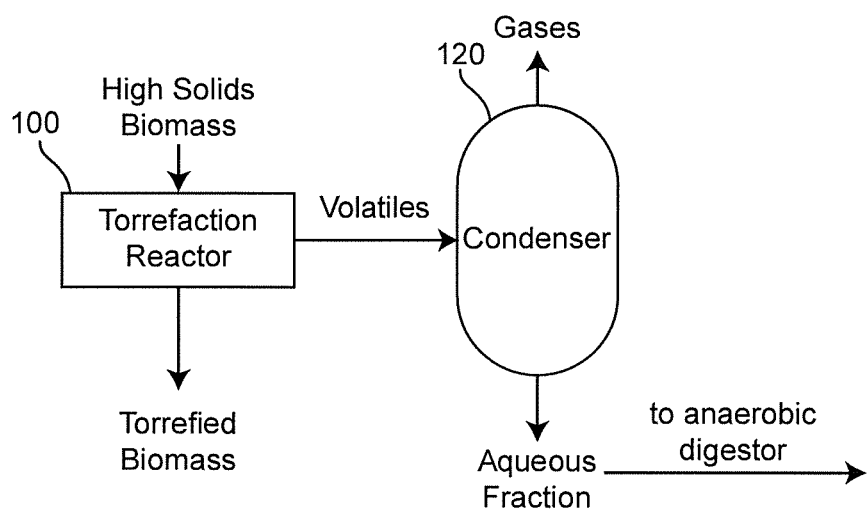
FIG. 2. Schematic illustration of a torrefaction reactor.

In certain embodiments, the thermochemical processing unit comprises a torrefaction reactor, as illustrated in FIG. 2. As shown in this figure, high solids biomass is fed into torrefaction reactor 100 and processed to produce torrefied biomass solids and volatiles. Volatiles are passed to condenser 120 where condensation of the volatiles takes place, producing 1) an aqueous fraction comprising light organic compounds and 2) gases. The aqueous fraction is transported to an anaerobic digester. The gases are combusted and may produce part of the energy consumed in the torrefaction process In this embodiment, there may only be a single condenser operable to produce a fraction of aqueous light organic compounds for digestion. However, the use of multiple condensers is not excluded.

Torrefaction reactors suitable for use in the present invention are known in the art. See, for example, issued U.S. Pat. No. 8,105,400 to Bergman, the complete contents of which is hereby incorporated by reference in entirety, and the references cited therein.

To date, much of the interest in developing torrefaction units has been driven by the desire to reduce grinding energy requirements to produce energy dense biomass for co-combustion with coal in power plants. Herein, systems with only a torrefaction reactor optionally provide a biomass solid suitable for combustion. In some embodiments, this torrefied biomass is treated in a manner suitable to yield a pellet or briquette (or other suitable form) for combustion, e.g. in a power generation plant or heating system.

As described herein, the light oxygenated organic compounds produced by torrefaction are condensed and used as a carbon source for methane production by co-digestion in anaerobic digesters. However, in some embodiments, a portion of the light oxygenated organic compounds are combusted to generate part of the heat needed to operate the torrefaction unit (e.g. see Bergman et al. 2005, Bridgeman et al. 2008, Deng et al. 2009, Prins et al 2006a, b, each of which are herein incorporated by reference), or for another purpose (e.g. to heat a pyrolysis unit in a combination system as described below, or for some other reason).

FIG. 2 provides a schematic illustration of a torrefaction unit which includes torrefaction reactor 100 and condenser 120. High solids biomass is fed into torrefaction reactor 100 and torrefied biomass and volatiles are produced. The volatiles are passed to condenser 120, which condenses the volatiles, producing an aqueous fraction as described herein, which is then sent to an anaerobic digester, and gases are then combusted and may produce part of the energy needed for the pyrolysis reactor.

Pyrolysis Reactors

Figure 3:
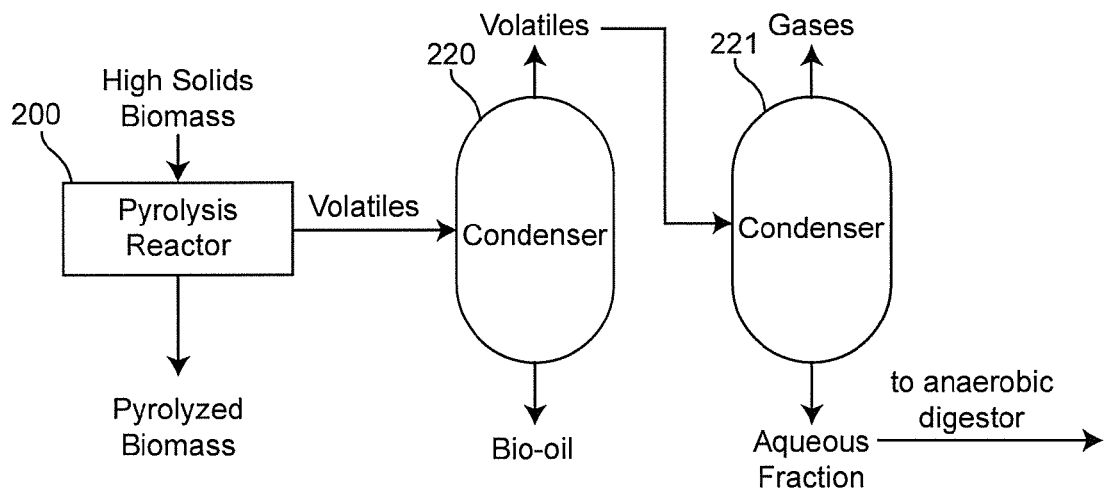
FIG. 3. Schematic illustration of a pyrolysis reactor.

In other embodiments, the thermochemical processing unit comprises a pyrolysis reactor, as illustrated in FIG. 3 or any alternative design (e.g., fixed bed, fluidized bed, circulating bed, ablative auger, rotary drums, moving beds, and auger). As shown in FIG. 3, high solids biomass are fed into pyrolysis reactor 200 and processed therein to yield pyrolyzed biomass solids (which may be referred to as "bio-char") and volatiles, which enter first condenser 220 where condensation produces bio-oil and volatile gases. High solids biomass is usually pretreated by grinding prior to being fed into the pyrolysis reactor, in order to compact the biomass and to facilitate the reaction process. Volatile gases are passed to second condenser 221 where condensation of the same produces 1) an aqueous fraction comprising light organic compounds and 2) gases are then combusted to, for example, produce part of the energy needed to run the thermochemical reactor.

The aqueous fraction is transported to an anaerobic digester. In some embodiments, multiple (i.e., a plurality) of condensers (e.g., from about 2 to about 10, i.e., 2, 3, 4, 5, 6, 7, 8, 9, or 10, i.e., a third, fourth, fifth, sixth, seventh, eighth, ninth, or tenth, etc.) may be utilized to collect discrete fractions of the organic compounds generated from the pyrolysis e.g. as illustrated in FIG. 3, first condenser 220 collects a bio-oil and second condenser 221 collects aqueous light organic compounds. In some embodiments, an array of in line condensers is employed and condenser operating conditions for each condenser (e.g. temperature, heating, cooling, pressure, etc.) are controlled so as to further fractionate the aqueous fraction into component organic compounds, by methods that are known to those of skill in the art.

Bio-oils produced by pyrolysis can be used directly or converted, for example, into transportation fuels or other useful substances e.g. via hydrotreatment, using methods which are known to those skilled in the art.

Pyrolysis reactors suitable for use in the present invention are known in the art, e.g. see, for example, those described in issued U.S. Pat. No. 8,153,850 to Hall, which lists Dynamotive Energy Systems (McLean, Va.) as a possible commercial source; and issued U.S. Pat. No. 8,119,076 to Keusenkothen, et al., the complete contents of both of which are hereby incorporated by reference in their entirety, as are the references cited therein.

Most of the existing pyrolysis units have one step condensation systems in which light oxygenated organic compounds are recovered together with heavier molecules (precursors of transportation fuels) in a crude bio-oil. The small molecules are responsible for many of the undesirable properties of such crude bio-oils. Although the separation of the light oxygenated organic compounds from the oil by using a two step condensation systems has been known for many years (Bunbury 1926, Oasmaa et al 2005, Westerhof et al 2007, 2011, each of which is herein incorporated by reference) and is a very promising strategy to enhance bio-oil quality, the lack of viable concepts to commercialize the light oxygenated organic compounds has heretofore represented a serious hurdle to the deployment of pyrolysis units with two steps condensation systems. The present invention solves this "problem".

FIG. 3 provides a schematic illustration of a pyrolysis unit which includes pyrolysis reactor 200 and condensers 220 and 221. High solids biomass is fed into pyrolysis reactor 200 and pyrolysis biomass and volatiles are produced. The volatiles are passed to condenser 220, which condensers the volatiles, producing bio-oil and volatiles (gases) which are passed to condenser 221. Condenser 221 creates an aqueous fraction as described herein, which is then sent to an anaerobic digester, and gases are combusted to generate part of the heat needed to operate the pyrolysis reactor.

Combination of Torrefaction and Pyrolysis Reactors

In yet further embodiments, the thermochemical processing unit (system) may involve a two stage reactor system wherein a first stage is torrefaction and a second stage is pyrolysis. In this embodiment, a first step of torrefaction has been added to reduce grinding energy which is otherwise usually expended e.g. to reduce biomass volume and/or to provide the biomass in a form that is easy to handle and readily amenable to pyrolysis. The step of torrefaction may replace grinding altogether, or may provide a torrefied biomass product that is more easily ground, thereby decreasing the energy required to prepare the biomass for pyrolysis.

Figure 4:
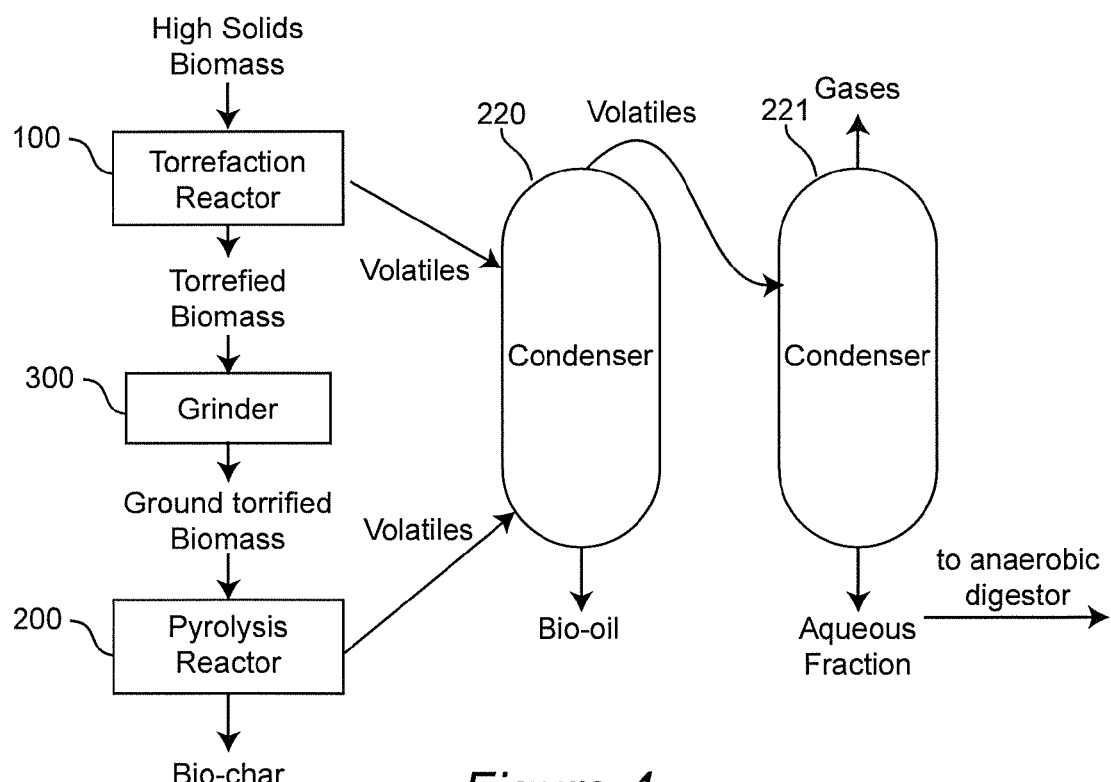
FIG. 4. Schematic illustration of a combined thermochemical reactor unit comprising both a torrefaction reactor and a pyrolysis reactor.

This embodiment is illustrated schematically in FIG. 4, which shows high solids biomass being fed into torrefaction reactor 100 to create torrefied biomass and volatiles. The torrefied biomass is processed by (optional) grinder 300 prior to being passed to pyrolysis reactor 200, which produces bio-char and volatiles. Volatiles from both torrefaction reactor 100 and pyrolysis reactor 200 are sent to first condenser 220, where bio-oil and volatiles are produced. The volatiles from first condenser 220 are passed to second condenser 221, which produces an aqueous fraction for anaerobic digestion as described herein, and gases are combusted to produce part of the energy needed to operate the system.

Transfer System

The light organic compounds obtained in torrefaction and/or pyrolysis units are transported to a location where anaerobic digestion will be carried out. The location may be adjacent or in close proximity to the thermochemical reaction unit(s) (e.g. within about 1, 2, 3, 4, or 5 miles), or may be located at a distance (e.g. 10 or more miles). Those of skill in the art will recognize that many types of transport systems exist for aqueous fractions as described herein. For example, if the thermochemical processing unit(s) is/are co-located with the anaerobic digester(s), e.g., in a remote location such as in a rural agricultural setting, the connections between the two may be made via a system of pipes, valves, pumps, etc., which transport the aqueous fraction a relatively short distance to the anaerobic digestion unit. Typically, the actual connection may be between a condenser which is part of the thermochemical reaction unit, and the nearby anaerobic digester, since the condenser is where the byproducts are fractionated. In some embodiments, co-located anaerobic digesters may be "built in" to the thermochemical processing unit so that, for example, the aqueous fraction(s) comprising the organic molecules of interest (those to be digested) are fractionated directly into the digester.

In other embodiments, the thermochemical processing unit(s) is/are not co-located with the anaerobic digester(s), but is/are situated at a distance, e.g. greater than about 10 miles, or 50 miles, or 100 miles, or 500 miles, or more. In these embodiments, systems of pipes, etc. as described above may also be used, so long as they are adapted, by methods well known to those of skill in the art, for the distance. Alternatively, the aqueous fraction may be shipped or hauled to the digester, e.g. via a tank truck, by rail, etc. or by a combination of these. Those of skill in the art will recognize that the use of such transport means is not confined to digester located at a distance, as even co-located facilities may use such means if necessary or desired.

Co-Digestion in an Anaerobic Digester

The aqueous fraction(s) that is/are produced from thermochemical processing are further processed by anaerobic microbial digestion in an anaerobic digestion unit. Anaerobic digestion (degradation) systems are known in the art (see, for example, U.S. Pat. No. 8,153,006 to Fessler, et al.; U.S. Pat. No. 8,148,142 to Sapp, et al.; and U.S. Pat. No. 8,129,158 to Straeter, the complete contents of each of which is hereby incorporated by reference in entirety). The systems may be in the form of a tank, a vat, a holding pond or lagoon, reservoir, plug flow digester, etc. Any container or method of containment may be used, so long as the container is configured to receive the aqueous fraction produced as described herein, in a manner that allows suitable anaerobic microbes located therein to access and digest the light organic small molecules.

According to the invention, low solids biomass is provided to an anaerobic digester, together with an aqueous fraction (or a plurality of aqueous fractions) derived from thermochemical processing of biomass as described above. In certain embodiments, to generate low solids biomass, organic material may be fed into the digester as a solid or low moisture content solid and diluted with aqueous effluent from the digester and/or water from an external source to create low solids biomass. In a further embodiment, the low solid content biomass contains nitrogen and/or substances that form nitrogen, e.g., upon breakdown.

In some embodiments, the aqueous fraction is introduced in a manner that enhances a biochemical process occurring in the digester, for example: 1) at or near the point (location) of entry within the digester, and/or 2) at the time of introduction. In other words, the aqueous fraction is not simply allowed to flow into the digester randomly, but the position of its entry and/or the timing of entry is planned to coincide with the occurrence of at least one biochemical digestion process carried out by the microbes, in order to enhance (or at least not hamper) the digestion process. Such targeted dosing wherein the organic fraction is added at a particular point (or point) and/or time (or times) in the process of digestion provides a means to enhance digester function by, for example, minimizing bacterial retention time, increasing the bacterial population and accentuating the degradation kinetics of the bulk digester feedstock by supplying readily biodegradable substrate (which in turn increases bacterial population). Those of skill in the art will recognize that the particular details of targeted dosing depend on the type of anaerobic digester utilized in the system. In general, the introduction of light, aqueous oxygenated organic compounds to a digester should coincide with a spatial (or temporal) position that contains a significant methanogenic bacterial population.

It is anticipated that the co-digestion of light oxygenated organic compounds together with low solids biomass would be viable in or compatible with many different digester designs. In one embodiment, a plug flow type digester is used, allowing selective introduction of the aqueous fraction rich in light oxygenated organic compounds into the last section of the linear path of the digester, preferably near the middle or end sections where a methanogenic bacterial population that can directly utilize these organics most efficiently is present. Plug flow digesters and/or mixed plug flow detectors are known in the art (e.g. see U.S. Pat. No. 6,673,243 to Srinivasan, et al.; U.S. Pat. No. 7,563,371 to McCune-Sanders, et al.; U.S. Pat. No. 8,110,106 to Allen, et al., the complete contents of each of which is hereby incorporated by reference in entirety, including references cited therein). This will considerably reduce the required residence time inside the reactor. The end result is that, instead of using the whole volume of the reactor to digest the aqueous fraction molecules, as would happen if a standard complete mix digester is used, the molecules will use only a fraction of the digester and will stay in the reactor for only ~2 days. The methanogens, whose population is enhanced due to the presence of light oxygenated organic compounds in the end section of the anaerobic digester, could also be partially recycled back into the digester to enhance methanogenic activity from the very beginning, thereby improving overall volumetric performance and efficiency of the reactor. This approach compares favorably to building a second high rate digester that would do a 1-2 day digestion, because of the cost savings associated with not having to build new digesters. However, the use of second (third, fourth, further additional, etc.) reactors is not excluded, and may be desirable, depending on the location of the thermochemical processing facility, the resources available, etc. Thus, in other embodiments, a plurality of anaerobic digestion containers may be used, each of which has a preponderance of a different type or types of bacteria suitable for a particular stage or step of anaerobic digestion. In yet other embodiments, a single container may be used for the entire process, and suitable populations of microbes may be introduced into the reactor at various stages of digestion, and/or after the cycle is complete and the feedstock is spent.

Exemplary mixed plug flow reactors include but are not limited to a 20 day plug flow reactor.

Figure 5:
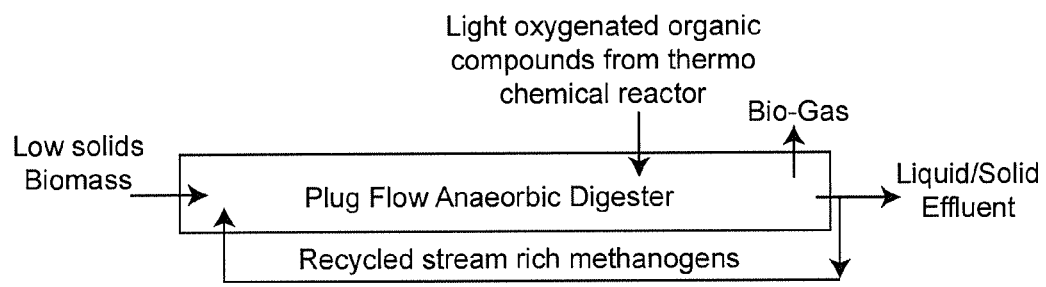
FIG. 5 shows the flow of materials into and out of an exemplary plug flow anaerobic digester.

FIG. 1, as described above, schematically illustrates the combined system. FIG. 5 illustrates the flow of materials when the anaerobic digester 500 is a plug flow type digester. As can be seen, low solids biomass and light oxygenated organic compounds from a thermochemical reactor are fed into the digester 500, with the light oxygenated organic compounds entering further downstream in the digester. Bio-gas (e.g. methane) is produced, as is a liquid and/or solid effluent rich in methanogens, which can be fed or cycled (recycled) back into the digester (indicated as the "Recycled stream rich in methanogens").

Exemplary Applications of the Technology

Anaerobic digestion of biomass traditionally yields methane, nutrient rich water and particulates and fiber. The methane produced by anaerobic digestion may be used in any suitable application. For example, the methane can be combusted to produce heat and energy to power and heat the digester and/or adjacent operations; burned to generate electricity; sold as a fuel; or used as feedstock for the production of hydrogen. In certain implementations, energy generated from the methane can be sold as electricity (Alatriste-Mondrago et al 2006). In particular implementations, the heat and energy can be used in co-located agricultural operations (e.g. refrigeration or processing of products from land and animals).

Figure 6:
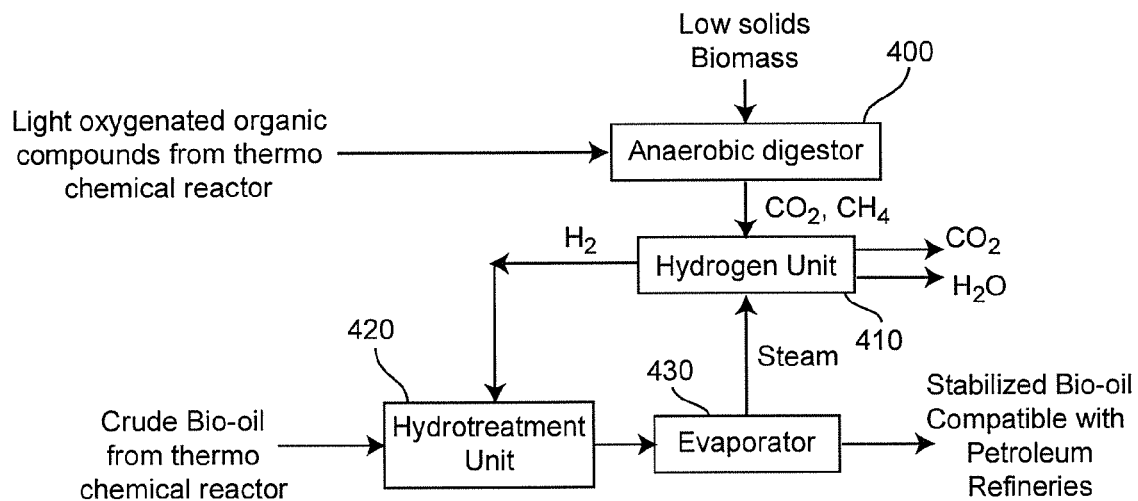
FIG. 6. Schematic illustration of an anaerobic digester coupled to a hydrogen generating unit, which produces $H_2$ for use in hydrotreatment of bio-oil.
Figure 7A:
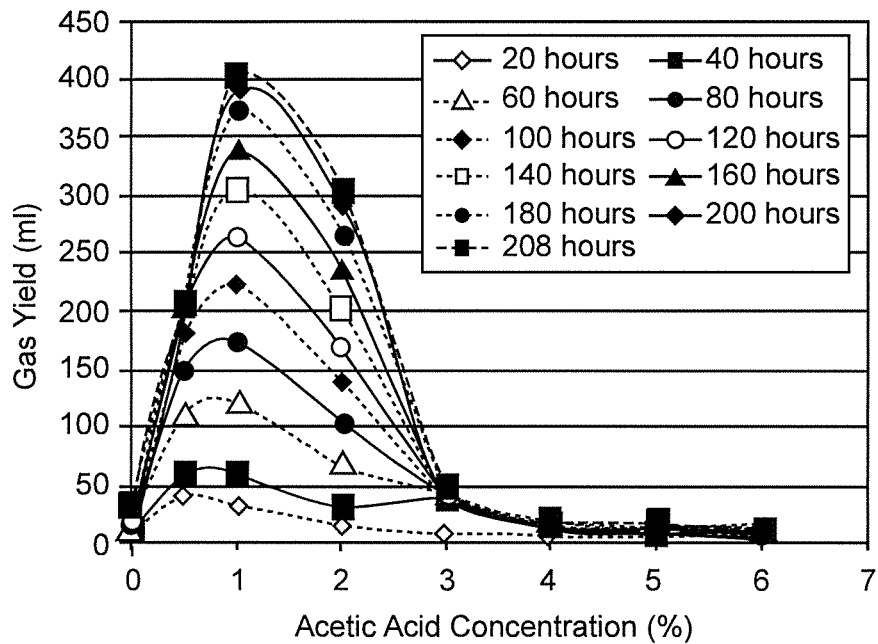
FIGS. 7A-D. Anaerobic co-digestion studied in a respirometer with molecules (acetic acid, formic acid, hydroxyacateladehyde and acetol) typically produced by the thermochemical processing of lignocellulosic materials.
Figure 7B:
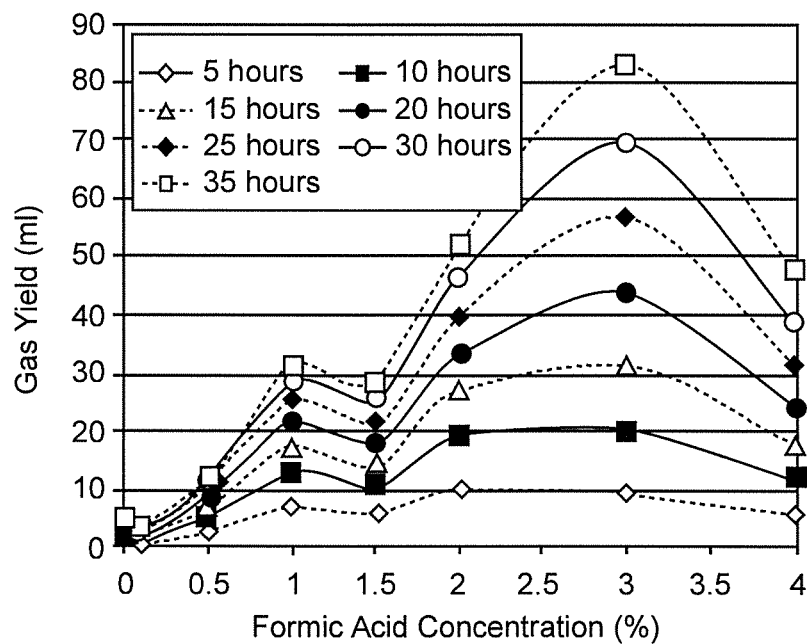
Figure 7C:
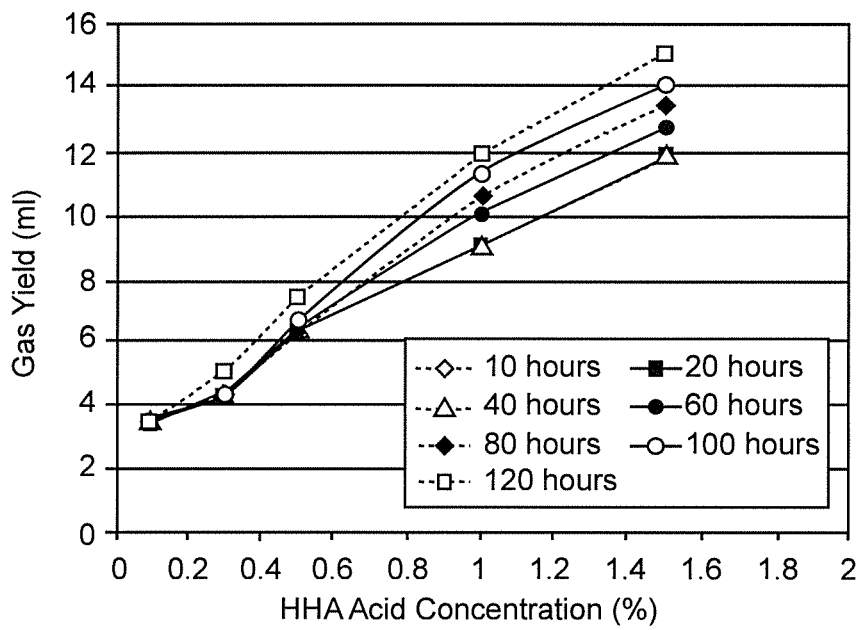
Figure 7D:
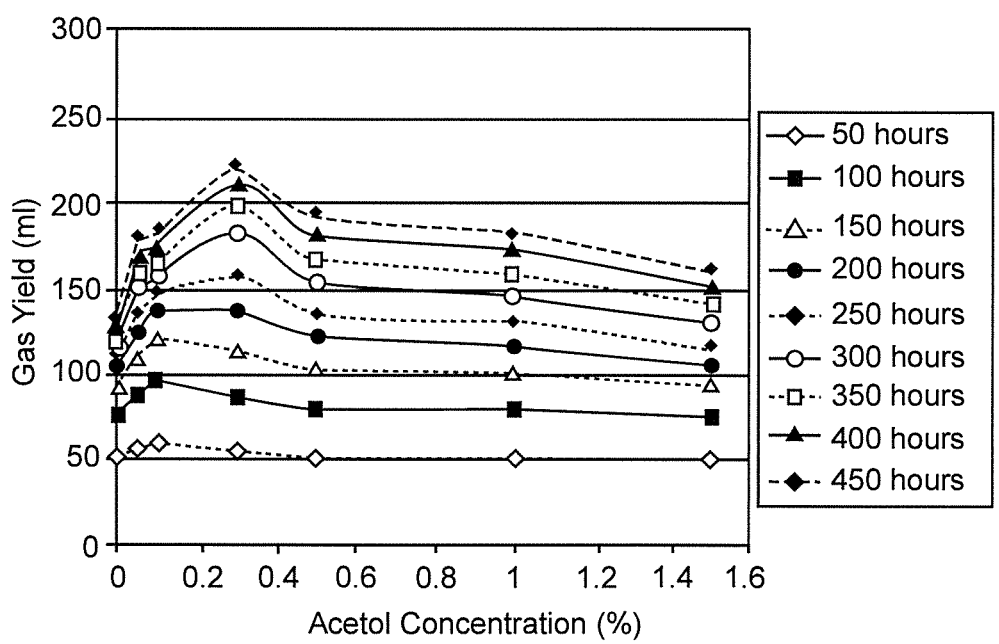

In some embodiments, the methane is used as feedstock for the production of hydrogen. Hydrogen can be produced from methane via steam reforming methods known in the art. This hydrogen may, in turn, be used for the hydrotreatment of crude bio-fuels (bio-oils, vegetable oils, etc.) for second generation bio-fuel production (See FIG. 6). FIG. 6 shows an exemplary scheme in which anaerobic digester 400 is coupled with hydrogen generating unit 410 (e.g. a steam reforming hydrogen generating unit) that uses the methane produced in anaerobic digester 400 to produce the hydrogen needed in a bio-oil stabilization step (mild hydrotreatment), which is carried out in hydrotreatment unit 420. The water formed in the stabilization step is evaporated in evaporator 430, leaving behind stabilized bio-oil. Steam produced by evaporator 430 may also be used, e.g. in hydrogen unit 410 to produce hydrogen, The fiber produced by anaerobic digestion can be extruded from the nutrient rich water to yield a high solid content biomass and used as feedstock for the thermochemical process (torrefaction, pyrolysis or gasification). The biochar produced in pyrolysis technologies can be used for the removal of nutrients (e.g. nitrogen and phosphorous)) from the aqueous waste streams of anaerobic digesters.

The combined thermochemical processing/anaerobic digester systems of the invention are well suited to be part of a new concept of or approach to biomass economy. For example, in some embodiments which pertain at least in part to the rural economy: (1) mobile and/or stationary pyrolysis units convert forest and agriculture biomass into a crude bio-oil rich in precursors of transportation fuels, an aqueous fraction rich in light oxygenated molecules, and bio-char; (2) rural refineries stabilize the heavy oils and produce methane, hydrogen and high value products, and (3) centralized petroleum refineries convert the stabilized bio-oil into green gasoline, jet fuel, diesel fuel, etc.

Rural refinery technology to stabilize crude bio-oils is comparable to (albeit with more rigorous requirements) than hydrotreatments currently used to produce xylitol and sorbitol. Economic viability and sustainability of this approach may depend on the ability or capacity to produce cheap hydrogen and high value products from bio-oil and bio-char. The methane that is produced from the co-digestion of manure and light oxygenated organic compounds from the pyrolysis of lignocellulosic materials is an excellent feedstock for the production of the hydrogen needed for bio-oil hydrotreatment to produce a stabilized bio-oil compatible with existing petroleum refinery standards.

Anaerobic digestion of biomass traditionally yields methane, nutrient rich water and particulates and fiber. The fiber can be extruded from the nutrient rich water to yield a high solid content biomass and the nutrients can, through chemical and/or physical means be extracted from the water. The methane produced herein can be combusted to produce heat and energy to power and heat the digester and/or adjacent operations. In certain implementations the energy generated can be sold as electricity (Alatriste-Mondrago et al 2006). In particular implementations the heat and energy can be used in co-located agricultural operations (e.g. refrigeration or processing of products from land and animals).

EXAMPLES

Example 1

Anaerobic Digestion Studies of C1-C4 Molecules Produced from the Pyrolysis of Lignocellulosic Materials Lignocellulosic material was pyrolyzed as described herein using a two-step condenser and the resulting aqueous phase was characterized. The results are shown in Table. 1. As can be seen, compounds known to be compatible with feeding of anaerobes for co-digestion as described herein were produced.

TABLE 1

Aqueous Phase Characterization

| Chemical Compounds | Mass % |
| --- | --- |
| Acetic Acid | 5.7 |
| Acetol | 3.5 |
| Formic Acid | 0.7 |
| Lignin derived compounds (UV-Vis) | 8.3 |
| Water content | 58.4 |
| Total | 76.6 |
| TOC | |
| Inorganic carbon | 0 |
| Total organic carbon | 6.4 |
| pH | 2.65 |

As shown in FIG. 7A-D, there are optimum concentrations for gas production during anaerobic digestion for each of the C1-C4 molecules produced during the thermochemical processing of lignocellulosic materials.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A system for the processing at least one biomass source comprising:
   at least one thermochemical reactor which degrades high solid content biomass;
   a fractional condenser system which condenses volatiles produced by the thermochemical reactor to produce an aqueous fraction containing light oxygenated organic compounds selected from the group consisting of formic acid, acetic acid, propionic acid, methanol, glycoaldehyde, and acetol;
   a transfer system to transport the aqueous fraction produced in the fractional condenser system; and
   an anaerobic digester which digests low solid content biomass and is configured to receive said aqueous fraction produced in said fractional condenser system from said transfer system at a spatial or temporal position between a middle and end section of said anaerobic digester which contains a methanogenic bacterial population,
   wherein the at least one thermochemical reactor includes a pyrolysis reactor.

2. The system of claim 1 wherein the pyrolysis reactor is configured to yield char and volatiles.

3. The system of claim 2 wherein the fractional condenser system comprises a first condenser configured to condense said volatiles to produce bio-oil and volatile gases, and a second condenser configured to condense said volatile gases to produce the aqueous fraction containing the light oxygenated organic compounds and gases suitable for combustion.

4. The system of claim 3, wherein said bio-oil is not transferred into the anaerobic digester.

5. The system of claim 3, wherein the anaerobic digester is configured such that at least a fraction of methane produced by the anaerobic digester is utilized to produce a chemical needed to up-grade the bio-oil produced by said first condenser.

6. The system of claim 1 wherein the fractional condenser system comprises a plurality of condensers each configured to concentrate a distinct product produced by the thermochemical reactor.

7. The system of claim 1 wherein the thermochemical reactor and condenser system are geographically isolated from the anaerobic digester.

8. The system of claim 7 wherein the transfer system is automotive, rail, air, pipeline and/or a combination thereof.

9. The system of claim 1 wherein the anaerobic digester is configured such that methane produced in the anaerobic digester is steam reformed to produce hydrogen.

10. The system of claim 9 further comprising means to direct said produced hydrogen for use in the hydrotreatment of a bio-oil.

11. The system of claim 1 wherein the thermochemical reactor is a two stage reactor comprising a first torrefaction stage and a second pyrolysis stage.

12. The system of claim 1 wherein the at least a fraction of the energy and/or heat produced is consumed by a co-located agricultural operation.

13. The system of claim 1 wherein the anaerobic digester is configured such that at least a fraction of the methane produced by the anaerobic digestion is burned to generate energy and/or heat.

14. The system of claim 13 wherein at least a fraction of the energy and/or heat produced is consumed by the thermochemical reactor.

* * * * *